United States Patent
Royds

(10) Patent No.: US 7,740,879 B2
(45) Date of Patent: Jun. 22, 2010

(54) ABUSE RESISTANT TRANSDERMAL DRUG DELIVERY PATCH

(75) Inventor: Robert B. Royds, Plainsboro, NJ (US)

(73) Assignee: Harrogate Holdings, Hamilton (BM)

( * ) Notice: Subject to any disclaimer, the term of this patent is extended or adjusted under 35 U.S.C. 154(b) by 1164 days.

(21) Appl. No.: 11/333,602

(22) Filed: Jan. 17, 2006

(65) Prior Publication Data

US 2007/0166233 A1   Jul. 19, 2007

(51) Int. Cl.
  A61F 13/00 (2006.01)
  A61F 13/02 (2006.01)
  A61L 15/16 (2006.01)

(52) U.S. Cl. .................. 424/449; 424/448; 424/443

(58) Field of Classification Search .......... None
  See application file for complete search history.

(56) References Cited

U.S. PATENT DOCUMENTS

| | | | |
|---|---|---|---|
| 3,062,209 A * | 11/1962 | Stowasser | 602/48 |
| 5,091,186 A | 2/1992 | Miranda et al. | 424/448 |
| 5,149,538 A | 9/1992 | Granger et al. | 424/449 |
| 5,236,714 A | 8/1993 | Lee et al. | 424/449 |
| 5,466,465 A | 11/1995 | Royds et al. | 424/449 |
| 5,667,798 A | 9/1997 | Royds et al. | 424/449 |
| 5,679,373 A * | 10/1997 | Wick et al. | 424/448 |
| 6,682,757 B1 | 1/2004 | Wright | 424/448 |
| 6,716,449 B2 | 4/2004 | Oshlack et al. | 424/449 |
| 7,316,817 B2 * | 1/2008 | Matloub et al. | 424/449 |
| 2004/0219195 A1 | 11/2004 | Hart et al. | 424/449 |
| 2004/0219196 A1 | 11/2004 | Hart et al. | 424/449 |
| 2005/0002997 A1 | 1/2005 | Howard et al. | 424/449 |
| 2005/0095279 A1 | 5/2005 | Gale et al. | 424/449 |

* cited by examiner

*Primary Examiner*—Isis A Ghali
(74) *Attorney, Agent, or Firm*—Watov & Kipnes, P.C.; Kenneth Watov

(57) ABSTRACT

A transdermal drug delivery patch has an excipient matrix containing an agonist for administration across the skin of a user, with the matrix further containing a plurality of spaced apart hollow cilia filled with an antagonist, whereby if an abuser attempts to physically remove the agonist the cilia will break releasing the antagonist, or if the abuser attempts to use a solvent to remove the agonist the cilia will dissolve releasing the antagonist, thereby blocking the effect the abuser is attempting to attain by concentrating the agonist for oral ingestion or by hypodermic needle injection.

22 Claims, 5 Drawing Sheets

ABUSE RESISTANT TRANSDERMAL DRUG DELIVERY PATCH

FIELD OF THE INVENTION

The present invention relates generally to transdermal drug delivery systems and devices, and more particularly to such systems and devices that are capable under normal use of providing the transdermal delivery of drugs, including agonists such as narcotic analgesics, and incorporating within the associated patch design the containment of an antagonist for release into the agonist to counter the use of a solvent or physical disruption to obtain illegal diversion of a narcotic agonist for a recreational narcotic user to obtain a "high."

BACKGROUND OF THE INVENTION

Transdermal drug dosage forms or devices are known in the art, and typically are provided via a patch that is adhesively attached to the skin by a user to cause an active therapeutic agent or agonist, often a narcotic opiate agonist or other analgesic, to diffuse from the patch through the skin for absorption into the bloodstream. The agonist then travels in the bloodstream to various areas of the body of the patient or user for alleviating pain or other adverse symptoms. In the case of opiate agonists, the main site of action is the central nervous system to relieve pain. An ever present problem with such transdermal drug delivery systems is that addicts and/or recreational drug users have developed methods for extracting the narcotic opiate from the transdermal drug delivery patch or device in order to orally or through injection deliver all of the narcotic opiate agonist into the body at the same time for obtaining a narcotic "high." Many attempts have been made to design transdermal drug delivery systems, such as transdermal patches, to counter or avoid such abuse. Extensive research is being pursued to accomplish this result.

SUMMARY OF THE INVENTION

In one embodiment of the invention, a percutaneous drug administration device, such as a therapeutic or transdermal patch, for example, provides for physical separation of a narcotic agonist from a narcotic opiate antagonist, with the antagonist being sequestered from release during normal use of the device. In this embodiment, a narcotic opiate agonist is incorporated into an excipient matrix which directly contacts the skin or mucosa when the associated patch is applied. A plurality of hair-like ciliate projections containing the required narcotic opiate antagonist are incorporated into the therapeutic matrix containing the narcotic agonist. A sufficient number of the cilia or a ciliate projections are included in the matrix, and are made sufficiently fragile, to cause the rupture thereof and resulting release of the contained narcotic antagonist if any attempts are made to physically remove the matrix to obtain an excessive dosage of the narcotic for recreational or illicit use by the abuser. Upon such release of the narcotic antagonist, it will mix with and disperse with antagonist in a manner negating the desired recreational effect. Also, in another embodiment of the invention, the composition of the cilia is selected to insure that if an abuser attempts to collect the narcotic agonist through use of a solvent, such action will cause the cilia to rapidly disintegrate or dissolve, resulting in the release of their contained narcotic antagonist.

In another embodiment of the invention, the outer patch container layer and integral ciliate projections are formed from the same material and filled with the narcotic antagonist, with the matrix containing the narcotic agonist filling the spaces between the ciliate projections. A circumferential flange is provided with a pressure sensitive adhesive to provide for firm attachment to the skin of a patient or user.

In another embodiment of the invention, the backing material for the transdermal patch is provided by a suitable plastic material in the form of a shell or outer backing layer, having a flange portion coated with a pressure sensitive adhesive. The material component providing the ciliate projections is secured within the plastic backing material or shell via use of an appropriate pharmacological adhesive, and is filled with the required narcotic antagonist. The excipient matrix containing the narcotic agonist is formed between the cilia as previously described. For each embodiment of the invention, the aforesaid matrix, with a patch applied to the skin, must be formed in a manner to insure that the matrix itself is in direct contact with the skin.

BRIEF DESCRIPTION OF THE DRAWINGS

Various embodiments of the present invention are described below with reference to the drawings, in which like items are identified by the same reference designations, wherein.

DETAILED DESCRIPTION OF THE PREFERRED EMBODIMENTS OF THE INVENTION

Figure 1A:
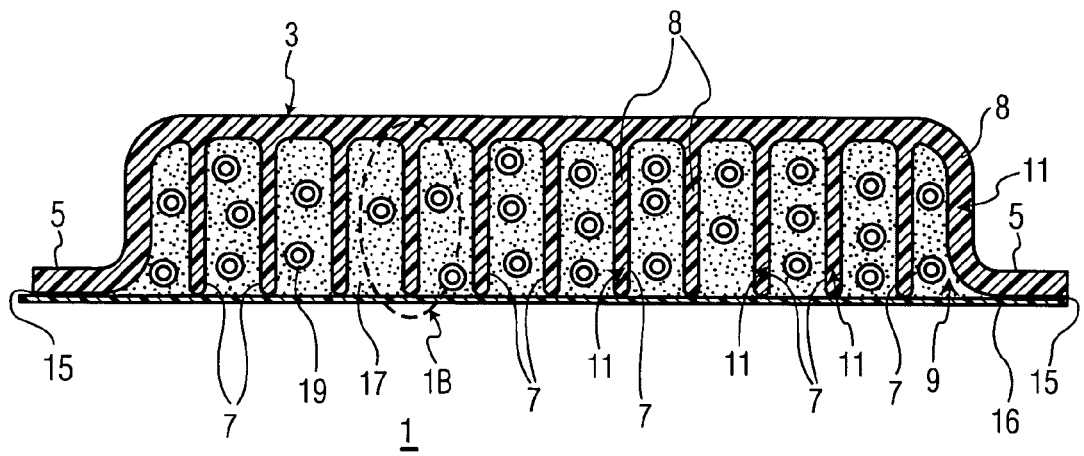
FIG. 1A shows a cross-sectional view of a transdermal patch for one embodiment of the invention.

A first embodiment of the invention is shown in cross-section in FIG. 1A. The transdermal patch 1 includes a container layer or main body 3 that is formed to provide a circumferential flange portion 5, and a plurality of spaced apart cilia 7 projecting into a cavity formed within the patch container 3, as shown. The patch container 3 includes a hollow core 11 throughout and within the ciliate projections 7, which are filled with a narcotic antagonist 8. The bottom portions of the circumferential flange 5 are coated with an appropriate pharmaceutical pressure sensitive adhesive 15, for insuring required securement of the patch 1 to the skin of a patient or user. The portions of the cavity 9 between the cilia 7 are filled with an appropriate excipient matrix 17 containing a desired narcotic agonist 19.

Figure 1B:
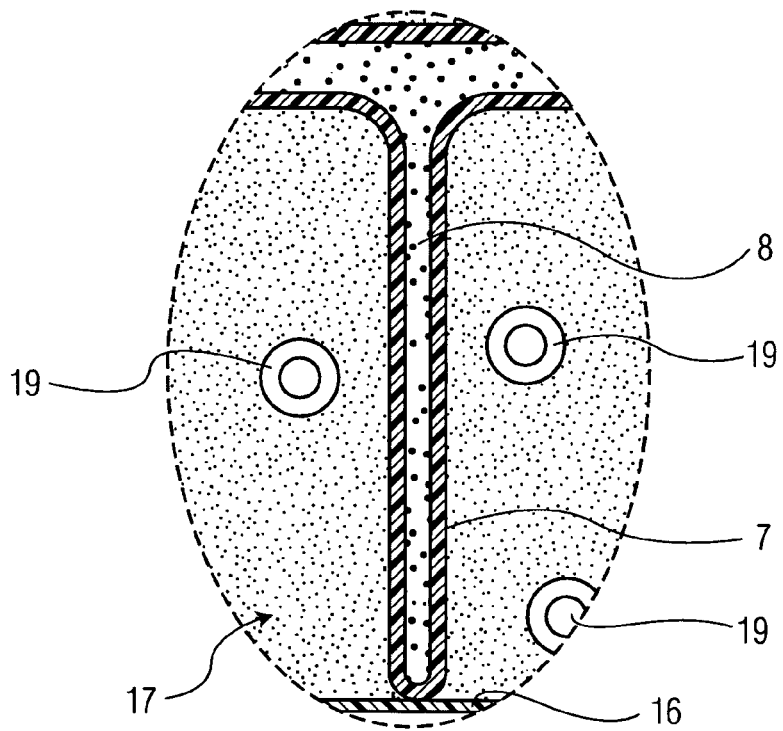
FIG. 1B shows an enlarged view of the encircled portion 1B of FIG. 1A.

The cilia 7, and associated container 3, are formed from a material that is thin and physically disruptive, and also soluble in known inorganic or organic solvents used by abusers for extracting the narcotic agonist 19. Accordingly, if an abuser tries to mechanically extract the narcotic agonist 19, the cilia 7 will rupture and release the narcotic antagonist 8 to counter the expected "high" of the abuser in attempting to concentrate the narcotic agonist 19. Similarly, if the abuser attempts to use an organic solvent to extract the narcotic agonist 19, the cilia 7 will dissolve, releasing their contained narcotic antagonist into the excipient matrix 17 and contained agonist 19. Note that in practice, the walls of the cilia 7 may be made thinner than the walls of the container 3 otherwise forming the integral outer portions and cilia 7 portions. FIG. 1B shows an enlarged view of a cilia 7 filled with narcotic antagonist 8 within an excipient matrix 17 containing agonist 19.

Figure 2:
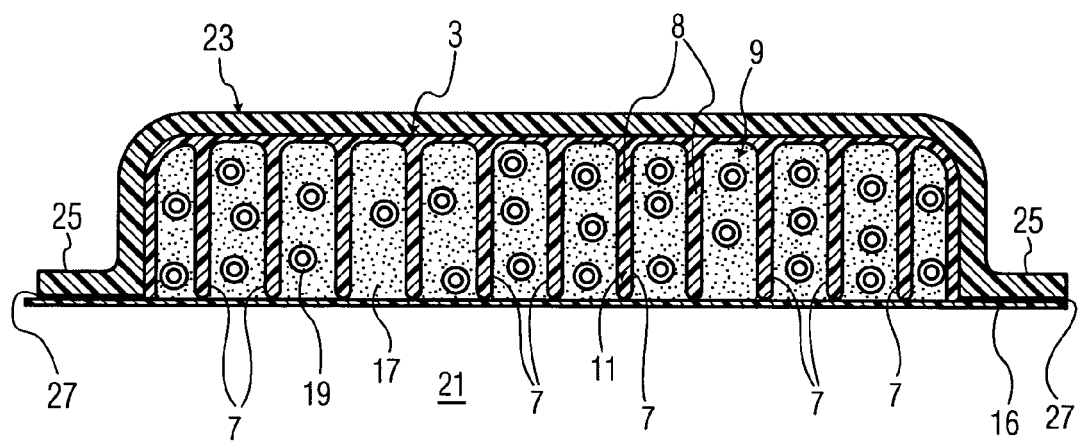
FIG. 2 shows a cross-sectional view of a transdermal patch for another embodiment of the invention.

In another embodiment of the invention, as shown in FIG. 2, a transdermal patch 21 includes an outer or backing layer 23 formed from an appropriate material, for example, that may be thin enough to be pliable for insuring that the excipient matrix 17 containing the narcotic agonist 19 is in close contact with the skin of a patient or user, as previously described. Material suitable for the outer or backing layer 23 can include elastomeric polymers such as polyether block amide copolymers, polyethylene methyl methacrylate block copolymers, polyurethanes, silicone elastomers, polyester block copolymers that are composed of hard and soft segments, rubber-based polyisobutylene, styrene, and styrene-butadiene and styrene-isoprene copolymers. Polymers that are flexible include polyethylene, polypropylene, and polyesters, e.g., polyester terephthalate, which may be in the form of films or laminates. The backing or outer layer 23 may also be comprised of a laminate of two or more of the aforementioned polymers, for example, a polyethylene/polyester laminate. The backing material or outer layer 23 will as indicated typically be thin enough to be very pliable, and will have secured to it the container 3 of FIG. 1A, except that the container 3 will now act as an inner bladder 3 with ciliate 7 containing narcotic antagonist 8, as previously described. The backing material 23 includes a circumferential flange portion 25, the bottom portions of which are coated with a known pharmaceutical adhesive 27, as shown. Other than the inclusion of the backing or outer layer 23, this second embodiment of the invention is substantially similar to the first embodiment of the invention of FIG. 1A, with an excipient matrix 17 containing agonist 19 being included between the ciliate 7.

The hollow core container 3 serving as the main body of the patch 1 of FIG. 1A, or an interior bladder of the embodiment of the invention of FIG. 2, is formed from a material that is soluble in typical solvents used by abusers in attempting to extract the narcotic agonist 19 from the patch 1 or patch 21. Such typical solvents include water, ethanol, ether, and mixtures thereof, and so forth. The container or bladder 3 can be formed from films made from a number of different materials, such as polyesters, polyethylenes, polyurethanes, polyvinyl acetates, and other known pharmaceutically useful materials. The bladder or container 3 can also be monolithically formed, or formed from multi-laminate layers of the material, for insuring that the antagonist will not be released from the cilia 7 during any incidental exposure to moisture for example, but will provide for rupture or dissolution of the cilia 7 when exposed to known solvents, as previously described. Also, know polymer based materials can be utilized where appropriate.

Note further in the embodiments of the invention of FIGS. 1A, 1B, and 2, the use of a peelable protection layer 16. As shown in the FIGS. 1A and 2, the peelable protection layer 16 covers the entire bottom portion or skin abutting portion of the patches 1 and 21, including the pressure sensitive adhesive 15 on flange 5 of patch 1, and the pressure sensitive adhesive 27 on flange 25 of patch 21. A user merely peels away the protective layer 16 from either the patches 1 and 21 to expose the pressure sensitive adhesive and the matrix 17 with agonist 19, for securing the patch 1 or 21 to the skin, as previously described.

The matrix 17 can in one embodiment be formulated to absorb multiple times its own weight in water, and can be provided by a number of materials, such as guar, acacia or xanthan gum, or a jelling agent or a polymer such as carboxypolymethylene, hydroxyethylcellulose or polyacrilamide, for example. Various matrix material is taught for transdermal patch use in the present inventor's U.S. Pat. No. 5,667,798, entitled "Transdermal Drug Delivery System," as issued on Sep. 16, 1997. The teachings of this patent are incorporated herein by reference to the extent that they do not conflict herewith. Other materials that can be utilized for the matrix 17 include micro-porous films of polyethylene or polypropylene.

The adhesive 15 of patch 1, and/or the adhesive 27 of patch 21, can be provided by any pharmaceutically acceptable pressure sensitive adhesive, such as, a polyacrylate, polysiloxanes, polyisobutylenes, silicone polymers, polybutadiene, and so forth, for example. By "pharmaceutically acceptable" is meant a material which does not interfere with the biological effectiveness of the drug being administered and which is not for any reason biologically or otherwise undesirable.

The agonist 19 for the patches 1 and 21 can be provided in the form of microcapsules as taught in the aforesaid U.S. Pat. No. 5,667,798. Alternatively, the agonist can be provided in a liquid form for absorption in the matrix 17.

The present invention is useful to prevent abuse of any opioid agonist for which there is an associated antagonist, which when combined therewith diminishes the effect of the opioid agonist to prevent abuse. Typical opioid agonists include but are not limited to morphine, cocaine, codeine, and so forth. An appropriate amount of the opiate antagonist is included in the cilia 7 for antagonizing the additive potential of the opiate analgesic drug 19 contained within the matrix 17. The amount of agonist used will depend upon the dosage requirements for the particular patch 1, as is known to those of skill in the art. As indicated, the amount of antagonist 8 incorporated into the cilia 7 must be sufficient for substantially reducing or preferably totally blocking the biological effects of the agonist being sought by the abuser. Opioid antagonists include and are not limited to naltrexone, naloxone, nalorphine, and pharmaceutically acceptable salts thereof, and mixtures thereof, for example. Numerous other antagonists 8 are known to those of skill in the art.

Figure 3B:
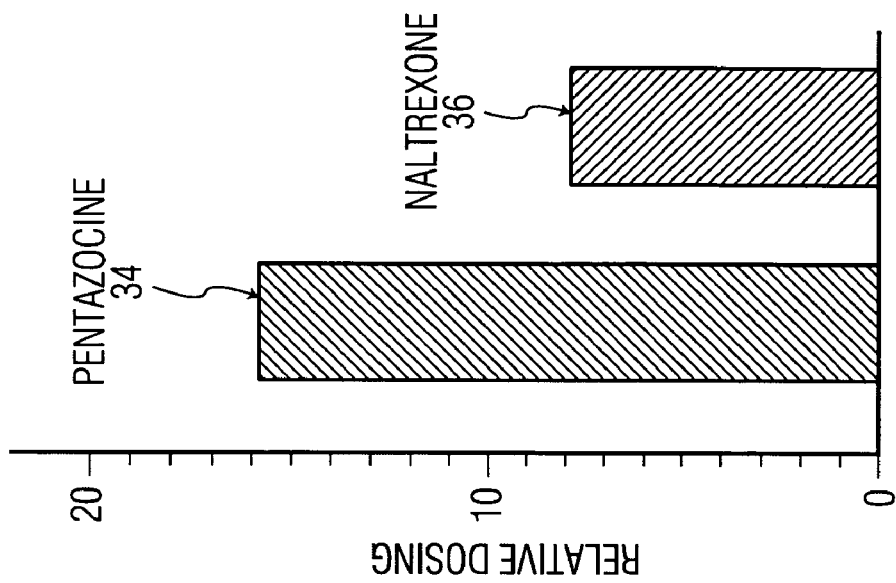
FIGS. 3A and 3B each show a bar graph of examples of relative dosing of quantities of antagonists required to block effects of particular agonists.
Figure 3A:
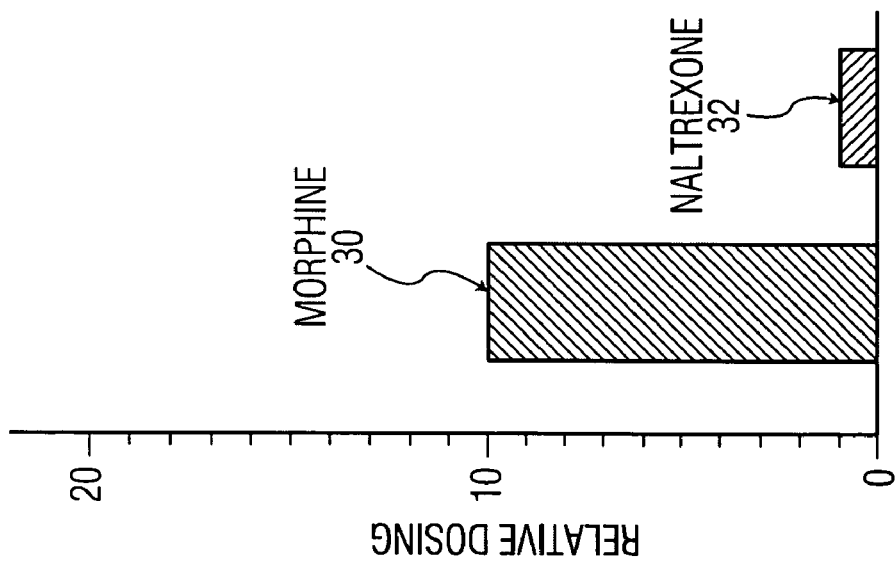
Figure 4:
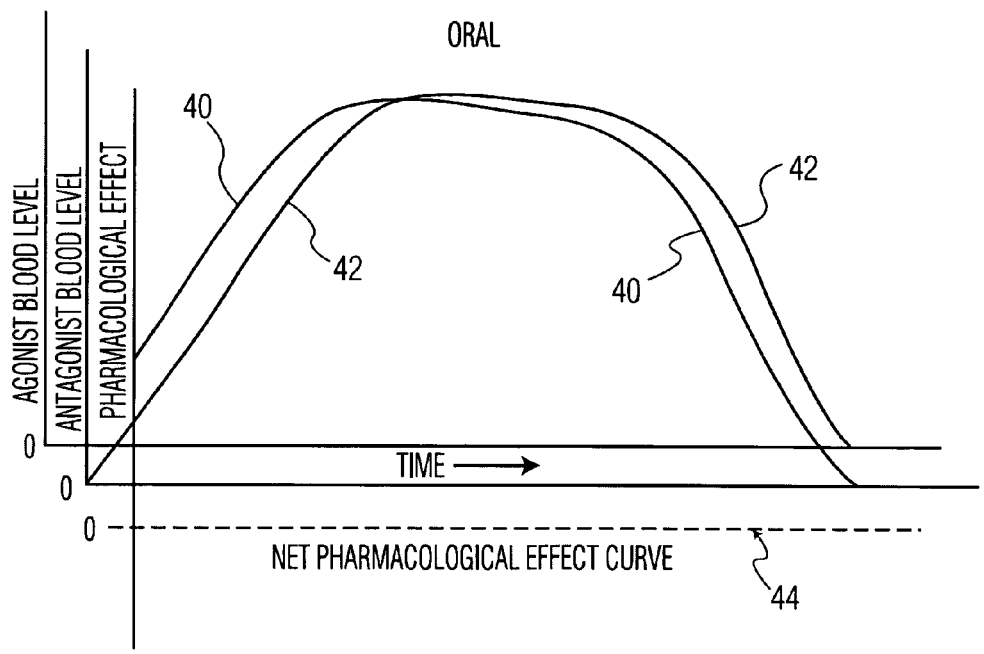
FIGS. 4, 5, and 6 show generalized graphs for bloodstream pharmacologic effect level vs. time examples for an agonist with a fast release profile as completely dampened by an antagonist release for oral, intravenous, and nasal routes of administration, respectively.
Figure 5:
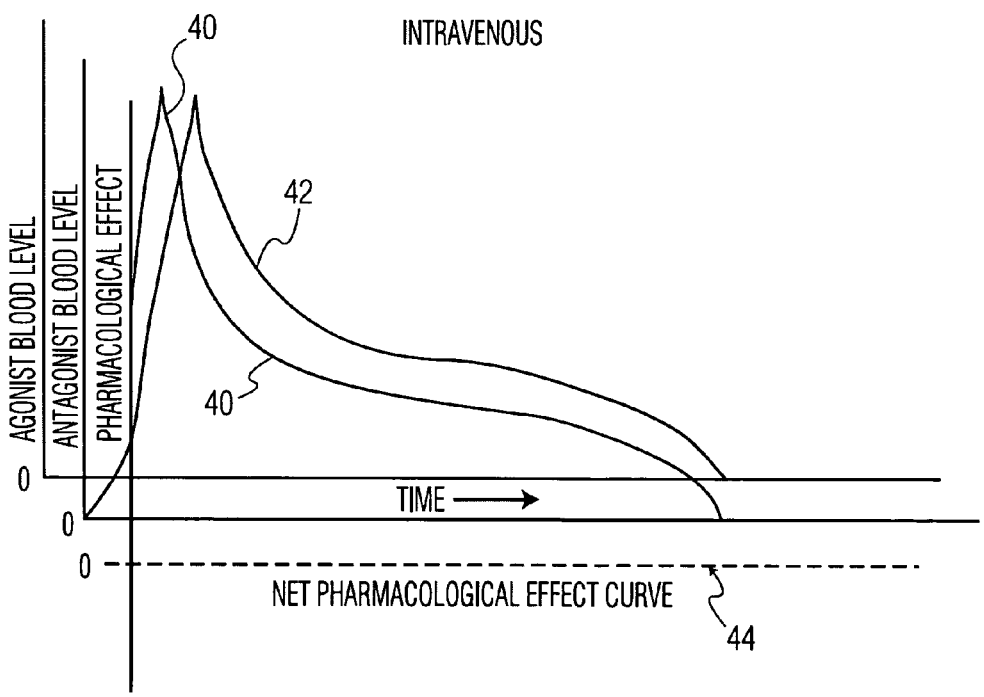
Figure 6:
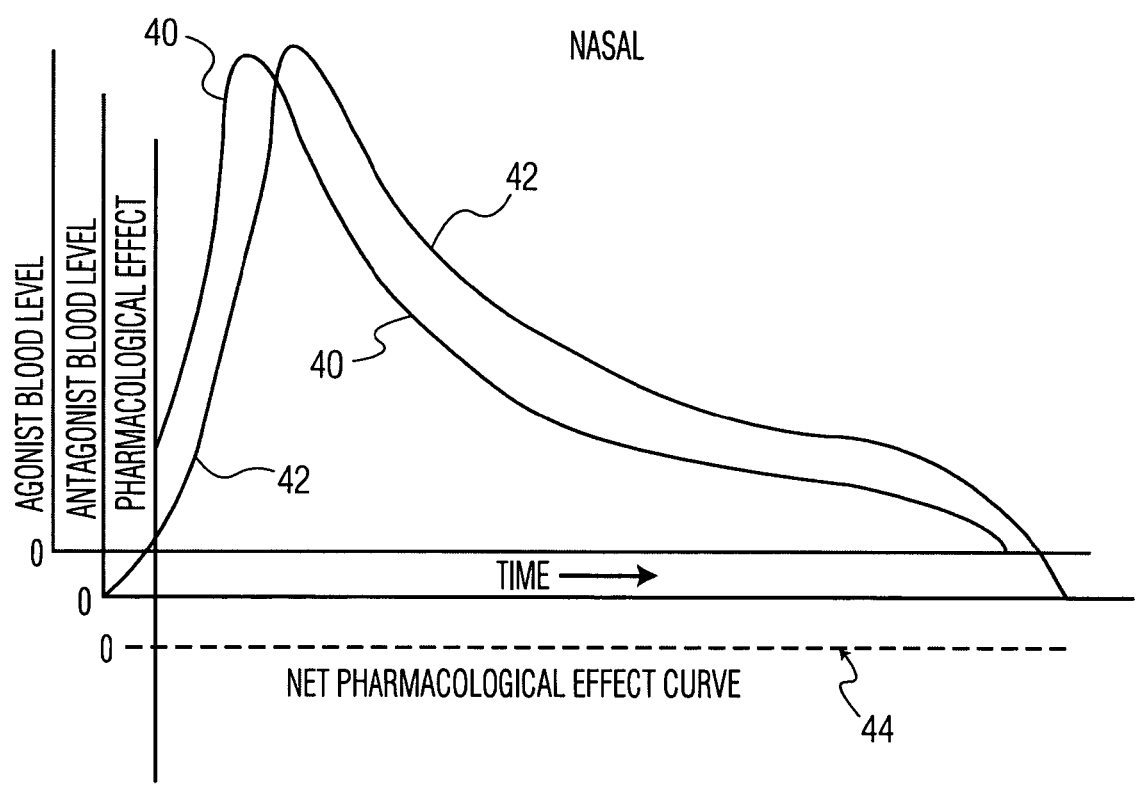

In FIG. 3A, an example is shown, in bar graph form, illustrating the relative dosing required to use naltrexone (antagonist) 32 to block the "high" effect of morphine (agonist) 30. FIG. 3B is a bar graph showing the relative dosing of naltrexone (antagonist) 36 to block the effect of pentazocone (agonist) 34. Also, FIGS. 4, 5, and 6 show graphs or curves developed by the inventor for illustrating the "Agonist Blood Level/Antagonist Blood Level/Pharmacological Effect" versus "Time" between an agonist 40 with a fast release profile that is countered by release of an antagonist 42, for providing a net pharmalogic effect 44 for oral, intravenous, and nasal drug administration, respectively, that completely eliminates the "high" effect sought by an abuser, in these examples.

Also as is known in the art, other antagonists 8 may include, nauseants, emetic substances, and foul tasting substances. Also, a hydrocolloid can be included in the cilia 7 which will swell in the presence of a solvent such as water to increase the viscosity of the solvent containing agonist that is extracted from the patch 1 to prevent an abuser from injecting the same via a hypodermic needle.

Example 1

For one illustrative example of a transdermal patch 1 as shown in the embodiment of the invention FIG. 1A, the patch 1 has a circular, square, rectangular, oval, or other appropriate configuration with a surface area of 5 to 50 cm$^2$ and a thickness sufficient enough to contain the chosen narcotic agonist. The hair-like cilia 7 may have a diameter ranging from 0.01 mm to 1.0 mm, whereas the remainder of the container or bladder 3, including the flange portions 5, will have a thickness ranging from 0.01 mm to 1.0 mm. The pressure sensitive adhesive 15 will have a thickness sufficient to securely adhere to the skin. The spacing between the cilia 7 will be within a range from $1/cm^2$ to $100/cm^2$. It is further expected that the cilia 7 are made rigid enough to permit easy insertion or pouring of the matrix 17 material therebetween. The agonist 19 will typically be homogeneously interspersed within the matrix 17 before installation of the matrix, or in the instance of the agonist 19 being in liquid form, can be injected into the matrix 17 after installation thereof. The peelable protection layer 16 is the last component to be installed for completing the patch.

Note that the peelable protection layer 16 can be provided by a polymeric material, which in a preferred embodiment is metalized. As is known in the art, such polymer materials include polypropylene, polyethylene, paper, and so forth.

Example 2

A patch 21, as shown in FIG. 2, can typically be provided in a circular square, rectangular, oval, or other appropriate configuration having a surface of 5 $cm^2$ to 50 $cm^2$, and a thickness ranging 0.001 to 0.05 inches for the main body 3. The backing or outer layer 23 can typically have a thickness ranging from 0.0005 to 0.003 inch. The hair-like cilia 7 may have a diameter ranging from 0.01 mm to 1.0 mm, whereas the remainder of the container or bladder 3, including the flange portions 25, will have a thickness ranging from 0.01 mm to 1.0 mm. The pressure sensitive adhesive 27 will typically have a thickness sufficient to securely adhere to the skin. The spacing between the cilia 7 will typically range from 0.01 mm to 1.0 mm. It is further expected that the cilia 7 are made rigid enough to permit easy insertion of the matrix 17 material therebetween. The agonist 19 will typically be homogeneously interspersed within the matrix 17 before installation of the matrix, or in the instance of the agonist 19 being in liquid form, can be injected into the matrix 17 after installation thereof. The peelable protection layer 16 is the last component to be installed for completing the patch.

Note that the peelable protection layer 16 can be provided by a polymeric material, which in a preferred embodiment is metalized. As is known in the art, such polymer materials include polypropylene, polyethylene, paper, and so forth, as is known in the art. The backing material 23 can have a thickness ranging from 0.002 to 0.007 inches.

Although various embodiments of the present invention have been shown and described, they are not meant to be limiting. Those of skill in the art may recognize certain modifications to these embodiments, which modifications are meant to be covered by the spirit and scope of the appended claims. For example, the narcotic agonist 19 can be replaced by an analgesic or other compound that is not a narcotic, but is nevertheless subject to abuse, whereby an appropriate antagonist will be used in the cilia 7.

What is claimed is:

1. A transdermal drug delivery patch for the delivery of a drug across the skin of a user comprising:
   a main body providing an occlusive covering on the skin of a user, including:
   an outer face;
   an inner face in combination with said outer face forming a hollow cavity below said inner face;
   a hollow core being formed between said outer and inner faces;
   a plurality of parallel elongated cilia projecting from said inner face into said hollow cavity, said plurality of cilia being spaced apart and each having a diameter along their lengths ranging from 0.01 mm to 1.0 mm, and a hollow tubular core extending from the hollow core formed between said outer and inner faces;
   an excipient matrix filling portions of said cavity between said plurality of parallel elongated cilia;
   an agonist contained in said matrix between said plurality of elongated cilia, respectively;
   an antagonist being contained both within the hollow tubular core of each of said plurality of cilia, respectively, and within the hollow core between said outer and inner faces, respectively;
   said plurality of cilia being rigid, and having thinner walls than the walls of said outer face, whereby upon rupture or dissolvement of said plurality of cilia by an abuser, said cilia will release their associated antagonist to block the desired effect an abuser is attempting to obtain by concentrating said agonist to ingest it orally or through injection; and
   means for securing said main body to a desired location on the skin of a user.

2. The patch of claim 1, wherein said securing means includes:
   a flange formed about the perimeter of said main body; and
   a pharmacological adhesive coated onto a bottom portion of said flange.

3. The patch of claim 2, further including:
   a peelable protective layer of material overlying said flange and matrix over an entire bottom portion of said main body.

4. The patch of claim 1, further including a backing layer or outer layer of material overlaying and secured to said outer face of said main body.

5. The patch of claim 4, wherein said securing means includes:
   said outer layer having a flange formed about its perimeter; and
   a pharmacological adhesive coated onto a bottom portion of said flange.

6. The patch of claim 5, further including:
   a peelable protective layer of material overlying bottom portions of said flange, and said main body.

7. The patch of claim 1, wherein said agonist is a narcotic agonist, and said antagonist is a narcotic antagonist.

8. The patch of claim 1, wherein said main body is formed from films made from materials selected from the group consisting of polyesters, polyethylenes, polymethanes, and polyvinyl acetates.

9. The patch of claim 2, wherein, said adhesive is selected from the group consisting of polyacrylate, polysiloxanes, polyisobutylenes, silicone polymers, and polybutadiene.

10. The patch of claim 1, wherein said excipient matrix is selected from the group consisting of guar, acacia, xanthan gum, jelling agent, carboxypolymethylene, polyethylene, and polypropylene.

11. The patch of claim 3, wherein said peelable protective layer is selected from the group consisting of polymeric material, metalized polymeric material, polypropylene, polyethylene, and paper.

12. The patch of claim 1, wherein said main body has a surface area ranging from 5 $cm^2$ to 50 $cm^2$, and a thickness between its inner and outer faces ranging from 0.001 inch to 0.05 inch.

13. The patch of claim 1, wherein said plurality of cilia are spaced within a range from $1/cm^2$ to $100/cm^2$.

14. The patch of claim 5, wherein said peelable protective layer is selected from the group consisting of polymeric material, metalized polymeric material, polypropylene, polyethylene, and paper.

15. The patch of claim 4, wherein the material for said backing or outer layer is selected from the group consisting of polyether block amide copolymers, polyethylene, methyl methacrylate block copolymers, polyurethanes, silicone elastomers, polyester block copolymers that are composed of hard and soft segments, rubber-based polyisobutylene, styrene, styrene-butadiene and styrene-isoprene copolymers, polyethylene, polypropylene, polyester terephthalate, and a laminate of two or more of the aforesaid.

16. The patch of claim 4, further including:
said main body having a surface area ranging from $5\ cm^2$ to $50\ cm^2$, and a thickness between its inner and outer faces ranging from 0.001 inch to 0.05 inch; and
said backing or outer layer having a thickness ranging from 0.0005 inch to 0.003 inch.

17. The patch of claim 4, wherein said agonist is a narcotic agonist, and said antagonist is a narcotic antagonist.

18. The patch of claim 15 wherein said main body is formed, from films made from materials selected from the group consisting of polyesters, polyethylenes, polymethanes, and polyvinyl acetates.

19. The patch of claim 5, wherein said adhesive is selected from the group consisting of polyacrylate, polysiloxanes, polyisobutylenes, silicone polymers, and polybutadiene.

20. The patch of claim 4, wherein said excipient matrix is selected from the group consisting of guar, acacia, xanthan gum, jelling agent, carboxypolymethylene, polyethylene, and polypropylene.

21. The patch of claim 6, wherein said peelable protective layer is selected from the group consisting of polymeric material, metalized polymeric material, polypropylene, polyethylene, and paper.

22. The patch of claim 4, wherein said plurality of cilia are spaced within a range from $1/cm^2$ to $110/cm^2$.

* * * * *